(12) United States Patent
Fumuro et al.

(10) Patent No.: US 8,128,571 B2
(45) Date of Patent: Mar. 6, 2012

(54) SPHYGMOMANOMETER

(75) Inventors: Shinichi Fumuro, Hikone (JP); Takeshi Kojima, Hikone (JP); Tsuyoshi Yuasa, Hikone (JP); Yoshitoshi Kanetsuna, Hikone (JP)

(73) Assignee: Panasonic Electric Works Co., Ltd., Kadoma-Shi, Osaka (JP)

( * ) Notice: Subject to any disclaimer, the term of this patent is extended or adjusted under 35 U.S.C. 154(b) by 1118 days.

(21) Appl. No.: 12/000,353

(22) Filed: Dec. 12, 2007

(65) Prior Publication Data
US 2008/0146948 A1 Jun. 19, 2008

(30) Foreign Application Priority Data
Dec. 14, 2006 (JP) ................. 2006-337374

(51) Int. Cl.
*A61B 5/02* (2006.01)
(52) U.S. Cl. .......... 600/499; 600/490
(58) Field of Classification Search .......... 600/485, 600/490, 495, 499; 606/201–203
See application file for complete search history.

(56) References Cited

U.S. PATENT DOCUMENTS

| | | | |
|---|---|---|---|
| 3,935,984 A * | 2/1976 | Lichowsky et al. | 600/499 |
| 5,069,219 A | 12/1991 | Knoblich | |
| 5,181,522 A * | 1/1993 | McEwen | 600/561 |
| 6,344,025 B1 * | 2/2002 | Inagaki et al. | 600/490 |
| 6,525,238 B2 * | 2/2003 | Corrales | 602/41 |
| 7,316,653 B2 * | 1/2008 | Sano et al. | 600/499 |
| 2002/0120199 A1 | 8/2002 | Ogura et al. | |
| 2004/0199081 A1 | 10/2004 | Freund et al. | |
| 2005/0187485 A1 | 8/2005 | Fumuro et al. | |
| 2005/0192501 A1 * | 9/2005 | Sano et al. | 600/499 |
| 2005/0283085 A1 * | 12/2005 | Inoue et al. | 600/499 |

FOREIGN PATENT DOCUMENTS

| | | |
|---|---|---|
| EP | 1 568 313 | 8/2005 |
| EP | 1 568 315 | 8/2005 |
| JP | 2004-254882 | 9/2004 |
| JP | 2005-237802 | 8/2005 |

OTHER PUBLICATIONS

Office Action in corresponding Japanese Application No. 2006-337374, dated May 31, 2011, and English summary thereof.

* cited by examiner

*Primary Examiner* — Miranda Le
*Assistant Examiner* — Meredith Weare
(74) *Attorney, Agent, or Firm* — Bacon & Thomas, PLLC

(57) ABSTRACT

A sphygmomanometer includes a cuff block having a cuff for restricting flow of blood and a base block, to which the cuff block is pivotably connected, having an elbow support for supporting an elbow of a user who inserts his/her arm into the cuff block. The sphygmomanometer further includes a compensating unit to compensate a change of distance from one end of the cuff block to the elbow support, which is caused by a pivotal movement of the cuff block with respect to the base block.

7 Claims, 8 Drawing Sheets

SPHYGMOMANOMETER

FIELD OF THE INVENTION

The present invention relates to a sphygmomanometer for measuring a blood pressure in an upper arm of a user.

BACKGROUND OF THE INVENTION

A blood pressure in an upper arm of a human cannot be precisely measured unless a cuff for restricting flow of blood tightens a proper portion of the upper arm when the cuff wraps around the upper arm. It is, however, difficult to position the cuff to a proper portion of the upper arm to measure a blood pressure.

Figure 8A:
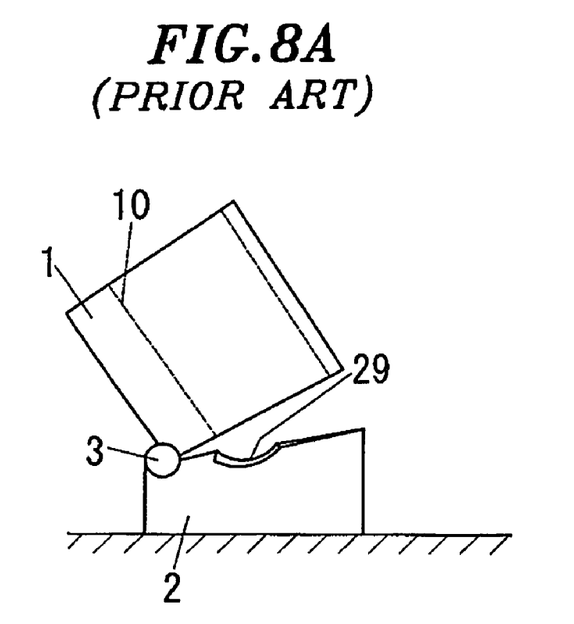
FIGS. 8A and 8B show schematic views of a conventional sphygmomanometer.
Figure 8B:
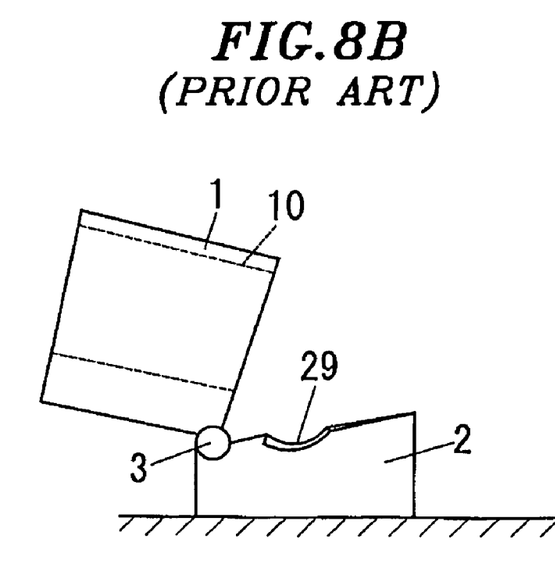

In this point, as shown in FIGS. 8A and 8B, there is a sphygmomanometer including a base block 2 to which a cuff block 1 having a cuff and a wearing cuff mechanism of the cuff is pivotably connected. Provided on the base block 2 is an elbow support 29 for supporting an elbow of a user who inserts his/her upper arm into an insertion hole 10 of the cuff block 1. In this case, the position of the cuff in the cuff block 1 can be set by placing the elbow on the elbow support 29.

However, since a part of one end of the cuff block 1 is pivotably connected to the base block 2 through a shaft 3, a distance from the one end of the cuff block 1 to the elbow support 29 varies depending on an angle of the cuff block 1 with respect to the elbow support 29, so that the position of the cuff with respect to the upper arm also varies (see, e.g., Japanese Patent Laid-open Application No. 2004-254882).

SUMMARY OF THE INVENTION

The present invention provides a sphygmomanometer capable of measuring a blood pressure in an upper arm of a user by positioning a cuff to a proper portion of the upper arm for the blood pressure measurement.

In accordance with an aspect of the present invention, there is provided a sphygmomanometer including a cuff block having a cuff for restricting flow of blood; a base block, to which the cuff block is pivotably connected, having an elbow support for supporting an elbow of a user who inserts his/her arm into the cuff block; and a compensating unit to compensate a change of distance from one end of the cuff block to the elbow support, which is caused by a pivotal movement of the cuff block with respect to the base block.

The change of the distance from the one end of the cuff block to the elbow support on the base block, due to the change of an inclined angle of the cuff block with respect to the base block, may be compensated by the compensating unit.

In this case, if the elbow support is provided in an elbow supporting block slidably supported on the base block, and if the elbow supporting block is connected to the cuff block and slides on the base block in accordance with the pivotal movement of the cuff block with respect to the base block, the compensation may be automatically performed.

The elbow supporting block may maintain its angle with respect to a horizontal plane substantially constant while it slides in accordance with the pivotal movement of the cuff block, or the elbow supporting block may change its angle with respect to a horizontal plane while it slides in accordance with the pivotable movement of the cuff block. The latter may allow a user to easily insert his/her arm through the cuff block and securely position the elbow.

Further, the elbow supporting block may include a forearm support for supporting a forearm of the user, and a wrist of the forearm supported by the forearm support is maintained at a lower level than the elbow supported by the elbow support. In this case, since the top surface of a table on which the base block is placed can be used as a support, a whole portion of the forearm may be supported without increasing the forearm support.

The sphygmomanometer may further include a lock mechanism to prevent the elbow supporting block from sliding with respect to the base block, so that the pivotal movement of the cuff block may be stopped and the sphygmomanometer may be easily carried.

If the elbow supporting block includes a guide shaft, the base block has a guide groove with which the guide shaft of the elbow supporting block is slidingly engaged, and the lock mechanism locks the guide shaft by positioning the guide shaft into a lock groove connected to the guide groove, the locking may be easily performed with a simple structure.

The base block is integrally formed with the elbow support, and the cuff block is pivotably attached to an end of the base block, the cuff block being slidable in a direction of changing a distance between the base block and the cuff block.

In accordance with another aspect of the present invention, there is provided a sphygmomanometer including a cuff block having a cuff for restricting flow of blood; and a gauge protruding from the cuff block and having one end adapted to contact with an armpit of a user who inserts his/her arm into the cuff block, a length of the gauge protruded from the cuff block being changeable.

With the sphygmomanometer in accordance with the embodiments of the present invention, the blood pressure can be measured precisely. More specific, since a change of the distance from the one end of the cuff block to the elbow support of the base block is compensated, the cuff can be positioned at a proper portion of the upper arm for the blood pressure measurement. Therefore, variation in position of the cuff, which is a factor deteriorating an accurate blood pressure measurement, can be prevented, so that the blood pressure can be measured precisely.

BRIEF DESCRIPTION OF THE DRAWINGS

The objects and features of the present invention will become apparent from the following description of preferred embodiments given in conjunction with the accompanying drawings, in which.

DETAILED DESCRIPTION OF THE PREFERRED EMBODIMENTS

Figure 1A:
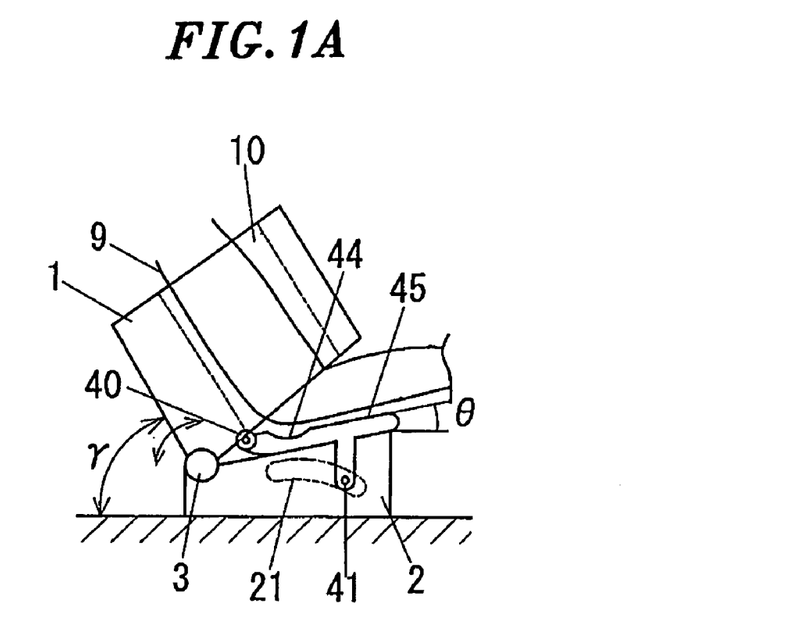
FIGS. 1A and 1B show schematic sectional views of a sphygmomanometer in accordance with an embodiment of the present invention.
Figure 1B:
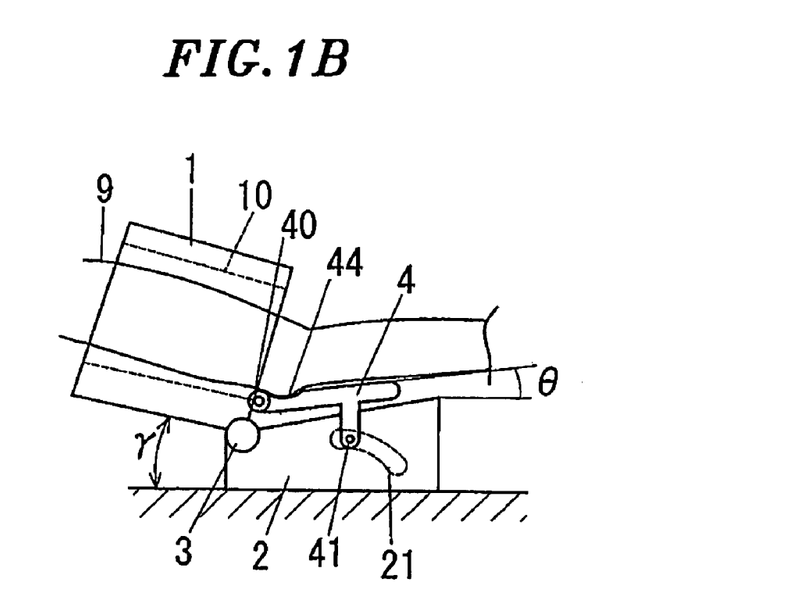

Hereinafter, preferred embodiments of the present invention will be described in detail with reference to the accompanying drawings. Referring to FIGS. 1A and 1B, a cuff block 1 includes a cuff and a wearing cuff mechanism which allows the cuff to wrap around an upper arm of a user. The cuff block 1 is of a cylindrical shape, wherein an insertion hole 10 penetrating through the cuff block is provided for inserting an upper arm. The cuff block 1 is pivotably connected to a base block 2 placed on a table through a shaft 3, so that a user can change an angle of his/her arm inserted into the insertion hole 10.

Further, on the top surface of the base block 2, has an elbow supporting block 4 is slidably provided. The elbow supporting block 4 includes an elbow support 44 for positioning an elbow of a user, and a forearm support 45 for supporting a forearm of a user. The elbow supporting block 4 is connected to the cuff block through a hinge shaft 40 at a position slightly offset from the shaft 3. Accordingly, when the cuff block 1 is pivotally moved with respect to the base block 2, the elbow supporting block 4 moves back and forward on the base block 2 in accordance with the pivotal movement of the cuff block 1. Therefore, a distance from one end of the cuff block 1 to the elbow support 44 is kept constant even though the cuff block 1 is pivotally moved.

Generally, in case a user, who inserts his/her upper arm 9 into the insertion hole 10 of the cuff block 1 for a blood pressure measurement, is relatively tall (or a height of a table on which the base block 2 is placed is relatively low), i.e., in case an angle $\theta$ between the cuff block 1 and a horizontal plane (an inclined angle of the cuff block 1) is comparatively large, the elbow supporting block 4 is positioned away from the shaft 3. On the contrary, when a user is relatively short (or a height of a table on which the base block 2 is placed is relatively high), i.e., in case the angle $\theta$ between the cuff block 1 and the horizontal plane (the inclined angle of the cuff block 1) is comparatively small, the elbow supporting block 4 is positioned close to the shaft 3.

Accordingly, a distance from the cuff of the cuff block 1 to the elbow support 44 of the elbow supporting block 4 on which a user positions his/her elbow is substantially kept constant regardless of the inclined angle of the cuff block 1. Therefore, an accurate blood pressure measurement can be performed at any time.

Moreover, the guide groove 21 provided in the base block 2 has an arc shape and one end thereof away from the shaft 3 is positioned at a lower position than the other end close to the shaft 3. (The guide groove 21 may have an inclined linear shape) This is for allowing the elbow supporting block 4 to move forward and backward in accordance with the pivotal movement of the cuff block 1 while the inclined angle $\theta$ of the elbow supporting block 4 is kept unchanged.

Figure 2A:
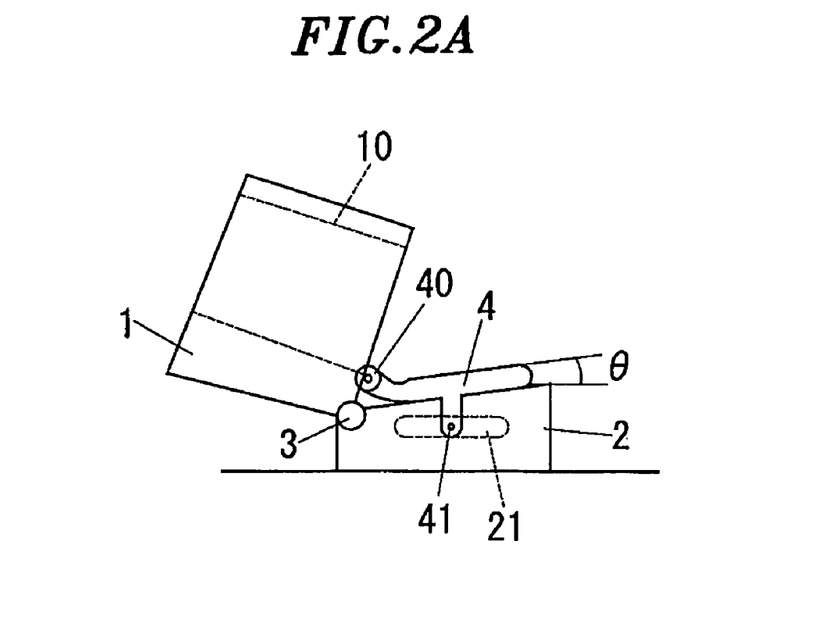
FIGS. 2A and 2B show schematic sectional views of another example of the sphygmomanometer in accordance with the embodiment of the present invention.
Figure 2B:
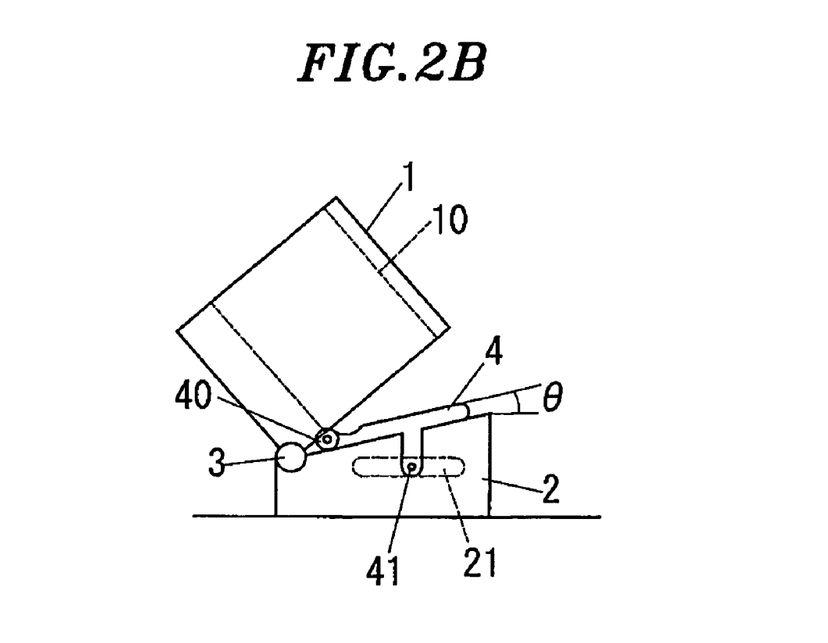

As shown in FIGS. 2A and 2B, the guide groove 21 may have a linear shape substantially parallel to the horizontal plane. In this case, when the elbow supporting block 4 slides in accordance with the pivotal movement of the cuff block 1, the angle $\theta$ of the elbow supporting block 4 is changed. However, when a user pivotally moves the cuff block 1 toward his/her chest in order to insert the arm through the insertion hole 10 of the cuff block 1 as shown in FIG. 2A, the angle $\theta$ of the elbow supporting block 4 becomes small and the top surface of the elbow supporting block 4 becomes horizontal.

Accordingly, the elbow supporting block 4 does not interfere with the arm of the user passing through the insertion hole 10. Further, since the angle $\theta$ of the elbow supporting block 4 can be increased when performing the blood pressure measurement, the user can position the elbow easily and securely.

Figure 3A:
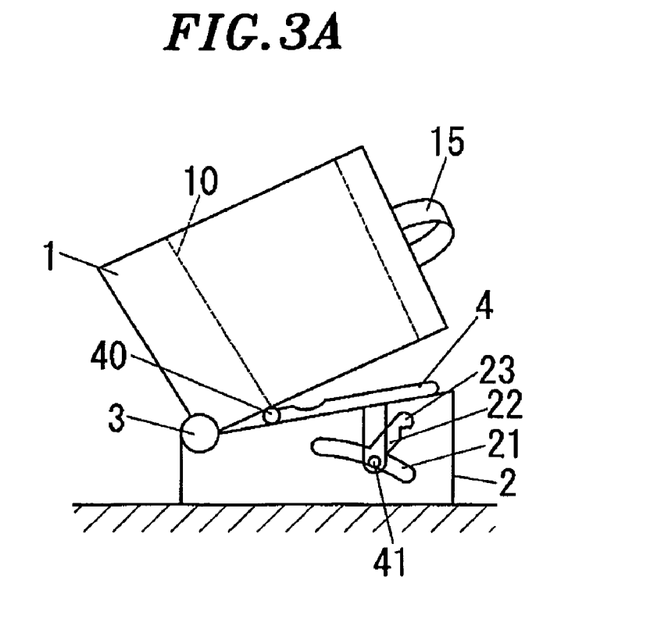
FIGS. 3A and 3B show schematic views of a modification of the sphygmomanometer in accordance with the embodiment of the present invention.
Figure 3B:
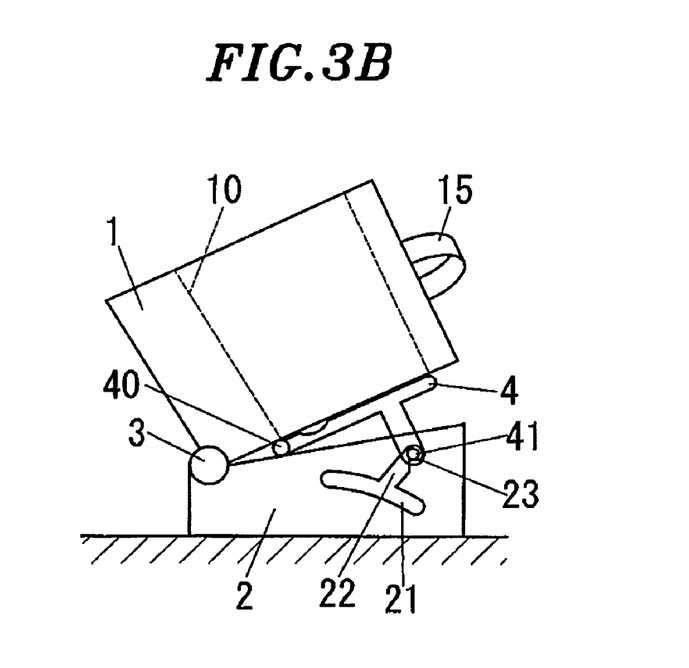

FIGS. 3A and 3B show a modification of the sphygmomanometer shown in FIG. 1, wherein a lock mechanism is provided thereto. The lock mechanism includes a lock groove 22 extended obliquely upwardly from a middle portion of the guide groove 21 of the base block 2. The cuff block 1 and the elbow supporting block 4 are lifted upward, such that the guide shaft 41 is moved into the lock groove 22 to be engaged with an engagement part 23 at a distal end of the lock groove 22. Therefore, the elbow supporting block 4 is locked, and the cuff block 1 is also in a locked state not to be pivotally moved. Reference numeral 15 in FIGS. 3A and 3B indicates a grip for holding the cuff block 1 by a hand to pivotally move the cuff block 1, and the grip is also used in carrying the sphygmomanometer in the locked state.

Further, in the locked state, the elbow supporting block 4 closes one end of the insertion hole 10 of the cuff block 1 so that any blood pressure measurement is prevented from being performed in the locked state, that is, in a state where an upper arm of a user cannot be maintained at a proper angle.

Further, the locked state is released by a user inserting his/her into the insertion hole 10 and lifting up the cuff block 1 while pushing the elbow supporting block 4 down, so that the insertion of the arm into the insertion hole 10 for the blood pressure measurement and the release of the locked state can be performed at the same time. Thus, no additional time is required for releasing the locked state.

Figure 4:
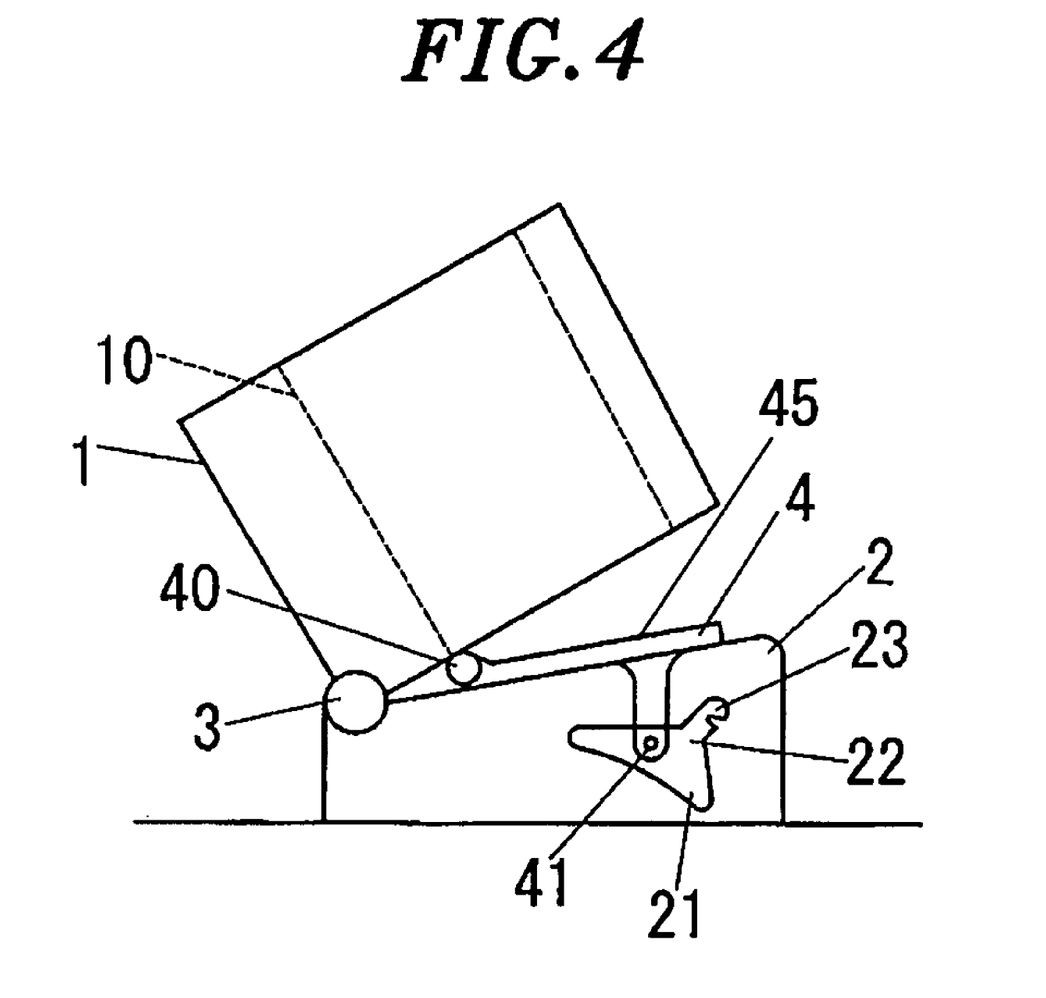
FIG. 4 shows a schematic view of another example of the modification of the sphygmomanometer shown in FIGS. 3A to 3B.

The lock groove 22 has an increased width on the side of the guide groove 21 as shown in FIG. 4. Therefore, the guide shaft 41 can move into the lock groove 22 to be engaged with the engagement part 23 from any position in the guide groove 21. Accordingly, the elbow supporting block 4 can be easily shifted to the locked state.

In the elbow supporting block 4, the elbow support 44 and the forearm support 45 are integrally formed. Accordingly, a forearm of a user is supported by the forearm support 45 and the user can maintain his/her arm in a comfortable state during a blood pressure measurement. Further, the forearm support 45 is configured to be inclined such that a wrist side thereof is higher (i.e., the angle $\theta$ has a positive value).

Figure 5:
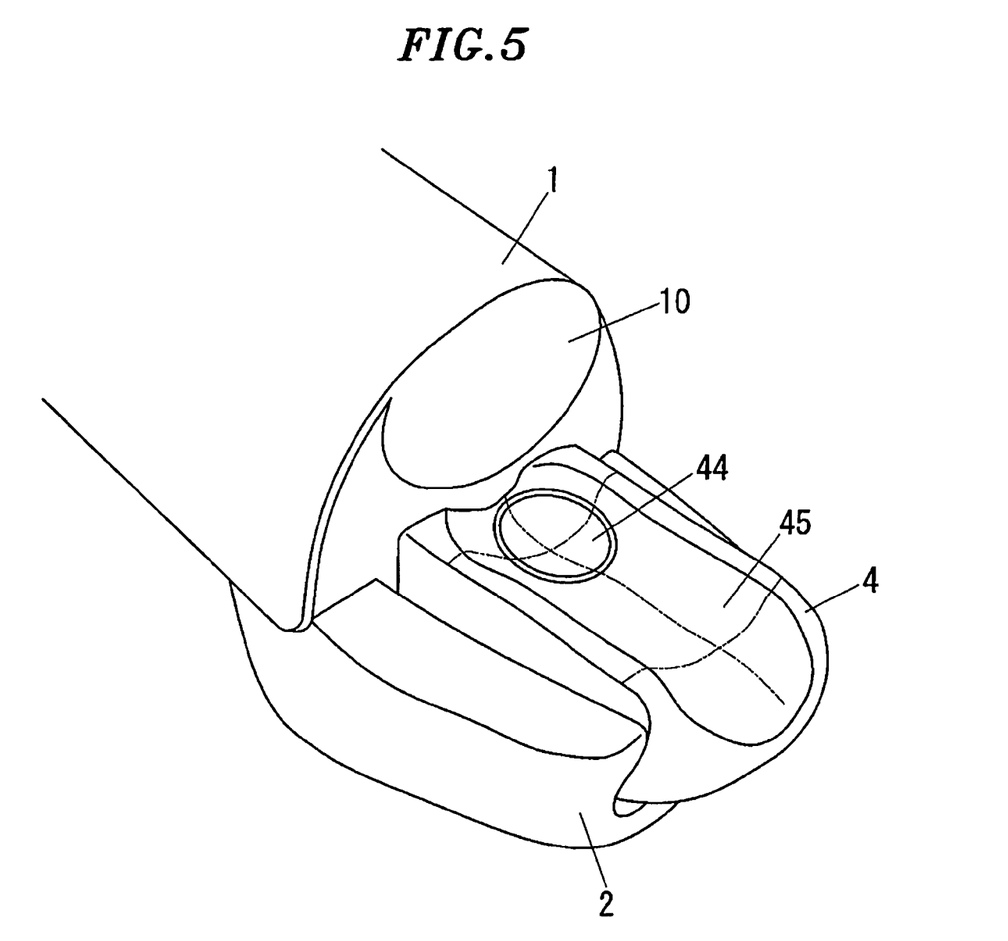
FIG. 5 shows a perspective view of still another example of the modification of the sphygmomanometer shown in FIGS. 3A and 3B.

Here, the forearm support 45 preferably supports the entire forearm. In this case, however, the forearm support 45 comes to be longer, thereby increasing the whole size. Therefore, as shown in FIG. 5, when the forearm support 45 is inclined to have an angle $\theta$ that makes the wrist side lower, the wrist of the forearm can be supported by the surface of a table on which the base block 2 is placed. Accordingly, the forearm support 45 is sufficient to support around the elbow, so that the whole size of the elbow supporting block 4 can be minimized while securely supporting the forearm.

In this case, the forearm support 45 is preferably made of a soft material such as a sponge, a foam rubber or the like rather than a hard material such as a plastic. Moreover, the elbow support 44 is preferably formed as a recess so that the position for placing the elbow is clear. Such a forearm support 45 described above can also be applied to a sphygmomanometer in which the elbow supporting block 4 is integrally formed with the base block 2.

Figure 6:
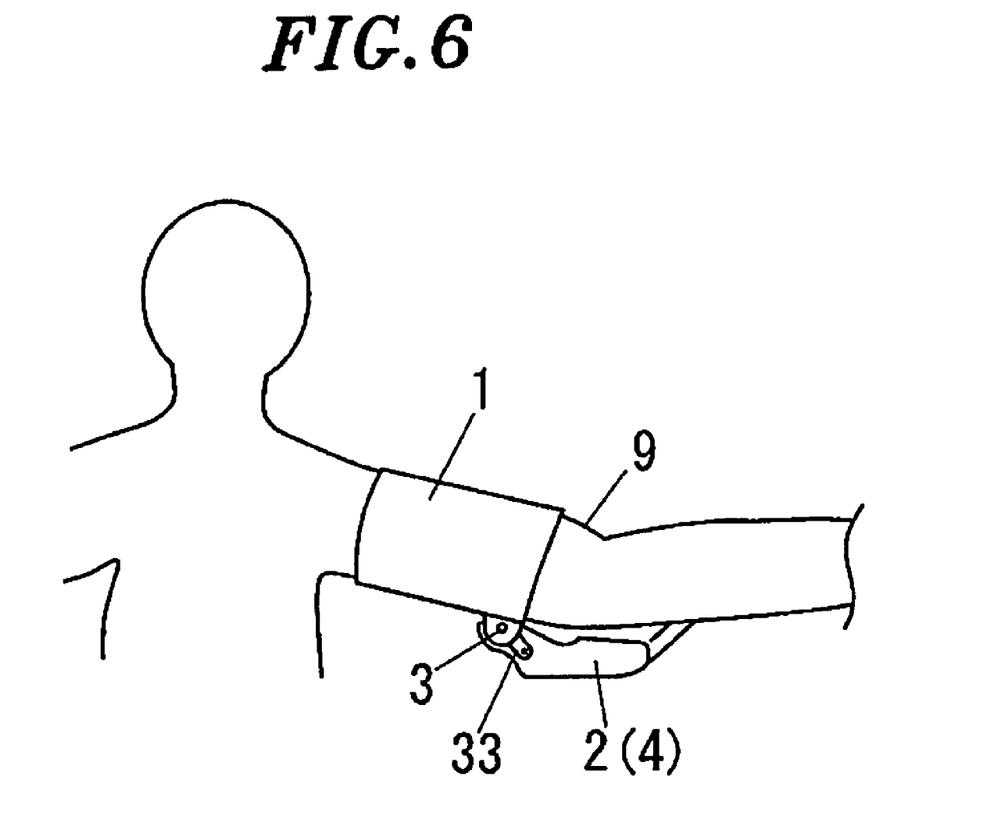
FIG. 6 shows a schematic view of a sphygmomanometer in accordance with another embodiment of the present invention.

FIG. 6 shows a sphygmomanometer in accordance with another embodiment of the present invention, wherein the base block 2 is configured to directly support an elbow and a forearm of a user. This corresponds to a sphygmomanometer in which the elbow supporting block 4 is integrally formed with the base block 2. The cuff block 1 is pivotably connected to the base block 2 through the shaft 3, and the shaft 3 can be shifted along a slide groove 33 formed in the base block 2 to change its position.

Therefore, when a user inserts his/her upper arm into the insertion hole 10 of the cuff block 1 and places the elbow on the elbow supporting portion of the base block 2, the user can adjust and maintain the angle between the cuff block 1 and the base block 2 properly and make the cuff block 1 positioned at a proper place of the upper arm for the blood pressure measurement.

Figure 7A:
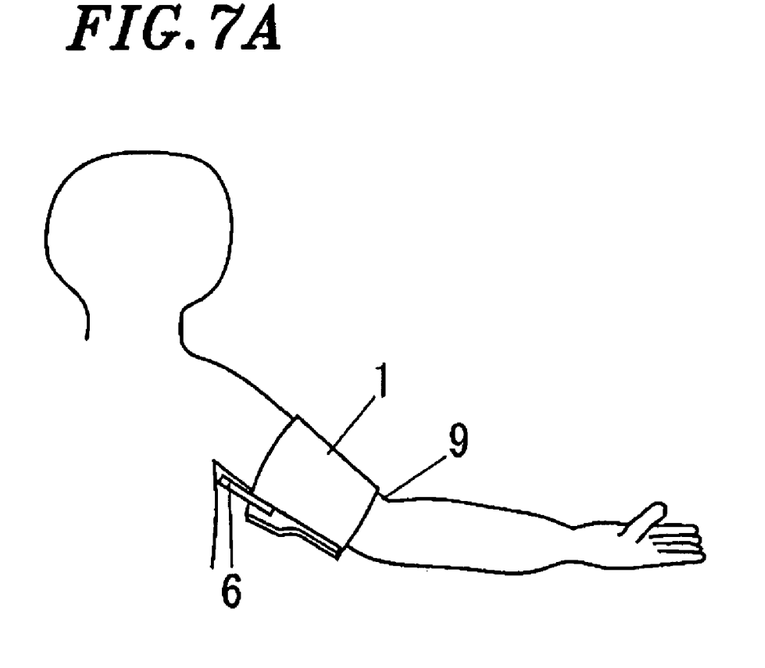
FIGS. 7A and 7B show a sphygmomanometer in accordance with still another embodiment of the present invention.
Figure 7B:
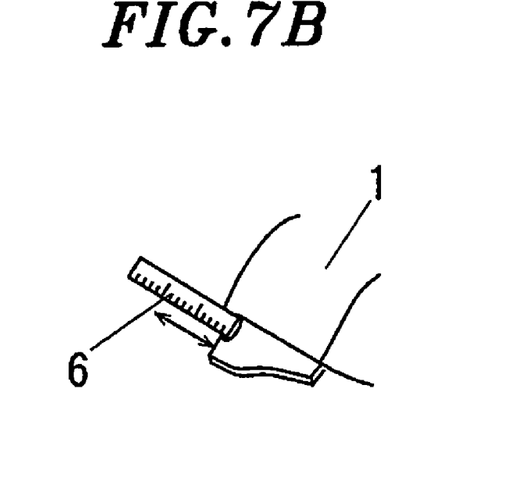

FIGS. 7A and 7B show a sphygmomanometer in accordance with still another embodiment of the present invention, wherein a rod shaped gauge 6 having one end, adopted to contact with an armpit of a user, protrudes from the cuff block 1. The gauge 6 is slidable in the direction parallel to an axial line of the insertion hole 10 of the cuff block 1.

After a protruding length of the gauge 6 is set by sliding the gauge 6 based on, e.g., the length of an arm of a user, the upper arm is inserted into the insertion hole 10 until the leading end of the gauge 6 contact the armpit. Accordingly, the cuff block 1 can be positioned at a proper region of the upper arm for the blood pressure measurement.

While the invention has been shown and described with respect to the preferred embodiments, it will be understood by those skilled in the art that various changes and modifications may be made without departing from the scope of the invention as defined in the following claims.

What is claimed is:

1. A sphygmomanometer comprising:
    a cuff block having a cuff for restricting flow of blood;
    a base block, to which to cuff block is pivotably connected, having an elbow support for supporting an elbow of a user who inserts his/her arm into the cuff block; and
    a compensating unit to compensate a change of distance from one end of the cuff block to the elbow support, wherein the change of distance is caused by a pivotal movement of the cuff block with respect to the base block,
    wherein the elbow support is provided in an elbow supporting block slidably supported on the base block, and the elbow supporting block is connected to the cuff block and slides on the base block in accordance with the pivotal movement of the cuff block with respect to the base block.

2. The sphygmomanometer of claim 1, wherein an angle of the elbow supporting block with respect to a horizontal plane is maintained substantially constant while the elbow supporting block slides in accordance with the pivotal movement of the cuff block.

3. The sphygmomanometer of claim 1, wherein an angle of the elbow supporting block with respect to a horizontal plane is varied while the elbow supporting block slides in accordance with the pivotable movement of the cuff block.

4. The sphygmomanometer of claim 1, wherein the elbow supporting block includes a forearm support for supporting a forearm of the user, and a wrist of the forearm by the forearm support is maintained at a lower level than the elbow supported by the elbow support.

5. The sphygmomanometer of claim 1, further comprising a lock mechanism to prevent the elbow supporting block from sliding with respect to the base block.

6. The sphygmomanometer of claim 5, wherein the elbow supporting block includes a guide shaft, the base block has a guide groove with which the guide shaft of the elbow supporting block is slidingly engaged, and the lock mechanism locks the guide shaft by positioning the guide shaft into a lock groove connected to the guide groove.

7. A sphygmomanometer comprising:
    a cuff block having a cuff for restricting flow of blood; and
    a gauge protruding from the cuff block and having one end adapted to contact with an armpit of a user who inserts his/her arm into the cuff block, a length of the gauge protruded from the cuff block being changeable,
    wherein the gauge is rod-shaped and indicates a length of the arm of the user.

* * * * *